United States Patent [19]

Atkinson et al.

[11] 4,348,398
[45] Sep. 7, 1982

[54] QUINOLINYL ETHANOLAMINES

[75] Inventors: Joseph G. Atkinson, Montreal; Burton K. Wasson, Ingleside, both of Canada

[73] Assignee: Merck Sharp & Dohme (I.A.) Corp., Rahway, N.J.

[21] Appl. No.: 219,728

[22] Filed: Dec. 23, 1980

[51] Int. Cl.$^3$ .................... A61K 31/47; C07D 215/22
[52] U.S. Cl. ...................................... 424/258; 546/155
[58] Field of Search .......................... 546/155; 424/258

[56] References Cited

U.S. PATENT DOCUMENTS

| 3,444,173 | 5/1969 | Goldman | 424/258 X |
|---|---|---|---|
| 3,644,353 | 2/1972 | Lunts et al. | 424/230 X |
| 3,705,233 | 12/1972 | Lunts et al. | 424/48 |
| 4,022,776 | 5/1977 | Nakagawa et al. | 424/258 X |
| 4,022,784 | 5/1977 | Nakagawa et al. | 424/258 X |
| 4,026,897 | 5/1977 | Nakagawa et al. | 424/258 X |
| 4,210,653 | 7/1980 | Baldwin et al. | 424/263 |

FOREIGN PATENT DOCUMENTS

| 54-16478 | 2/1979 | Japan | 424/258 |
|---|---|---|---|
| 1013224 | 12/1965 | United Kingdom | 546/156 |

OTHER PUBLICATIONS

Christol et al., Bull. Soc. CheChim. France, pp. 2313–2318, (1961).

Primary Examiner—Glennon H. Hollrah
Assistant Examiner—Diana G. Rivers
Attorney, Agent, or Firm—Daniel T. Szura; Martin L. Katz

[57] ABSTRACT

Heterocyclic ethanolamines of the formula

Het—CHOH—CH$_2$—NH—aralkyl where het is a 10 membered N heterocycle are disclosed. The compounds are useful as pharmaceuticals.

13 Claims, No Drawings

QUINOLINYL ETHANOLAMINES

BACKGROUND OF THE INVENTION

The present invention is concerned with heterocyclic compounds of the formula

Het—CHOH—CH$_2$—NH—aralkyl wherein Het is a quinolyl group.

Substituted phenylaminoethanols of the formula Ph—CHOH—CH$_2$—NH—aralkyl where Ph is a substituted phenolic group are disclosed in U.S. Pat. Nos. 3,644,353 and 3,705,233. These compounds have random activity as β-adrenergic stimulants and β-adrenergic blockers. These compounds are taught to be useful as pharmaceuticals for treating glaucoma and cardiovascular disorders such as hypertension and arrthymias.

Heterocyclic ethanolamines which have pharmaceutical utility have been discovered.

SUMMARY OF THE INVENTION

Heterocyclic compounds of the formula Het—CHOH—CH$_2$—NH—aralkyl where Het is a quinolyl group and their use as pharmaceuticals.

DESCRIPTION OF THE PREFERRED EMBODIMENTS

An embodiment of the present invention is compounds of the formula

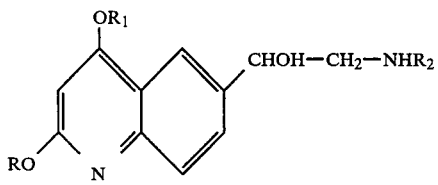
(I)

tautomers, and pharmaceutically acceptable salts thereof wherein

R and R$_1$ are independently selected from H and C$_1$–C$_3$ alkyl and

R$_2$ is

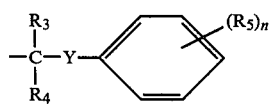

wherein
R$_3$ and R$_4$ are independently selected from H and C$_1$–C$_3$ alkyl,
R$_5$ is H, OH, OCH$_3$ halogen or C$_1$–C$_3$ alkyl,
Y is CH$_2$, (CH$_2$)$_2$, (CH$_2$)$_3$, (CH$_2$)$_4$ or —CH$_2$O— and
n is 1 or 2.

The pharmaceutically acceptable salts are the salts of the Formula I base with suitable organic or inorganic acids. Suitable organic acids include carboxylic acids such as acetic acid, pamoic acid, pivalic acid, oxalic acid, lauric acid, pelargonic acid, citric acid, tartaric acid, maleic acid, oleic acid, propanoic acid, succinic acid, isobutyric acid, malic acid and the like, the non-carboxylic acids such as isethionic acid and methane sulfonic acid. Maleic acid salts are preferred. Suitable inorganic acids are the hydrogen halides e.g. HCl, HI, HBr, phosphoric acid and sulfuric acid. The hydrohalide salts, and especially the hydrochlorides, are preferred. These salts can be prepared by treating the free base with an appropriate amount of a suitable acid, generally in a solvent.

R$_2$ is the phenalkyl group

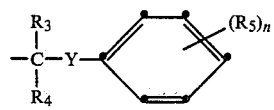

Each of R$_3$ and R$_4$ may be C$_1$–C$_3$ alkyl e.g. CH$_3$, C$_3$H$_7$, C$_2$H$_5$ and the like or hydrogen. CH$_3$ and H are preferred R$_3$/R$_4$ substituents while it is more preferred when one or both of R$_3$/R$_4$ is CH$_3$. Y is CH$_2$O, CH$_2$ or (CH$_2$)$_{1-4}$, with CH$_2$ and (CH$_2$)$_2$ being preferred. R$_5$ is H, OH, OCH$_3$, halogen (Br, Cl, I or F with Br and Cl being preferred) and C$_1$–C$_3$-alkyl, branched or linear. H and OCH$_3$ are preferred definitions of R$_5$.

Examples illustrating useful R$_2$ groups are

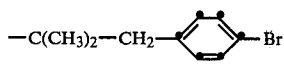

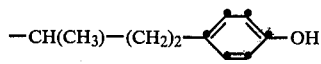

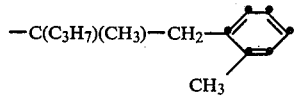

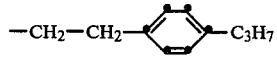

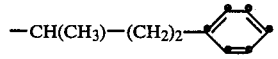

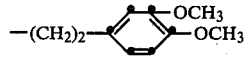

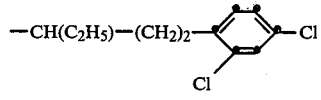

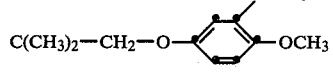

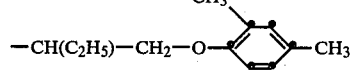

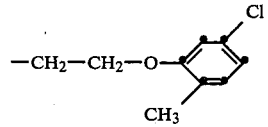

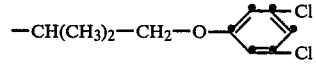

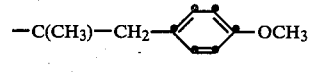

-continued

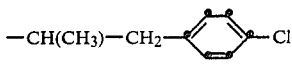

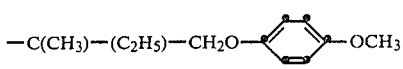

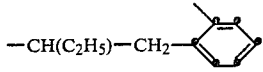

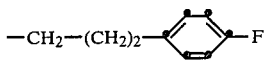

and the like.

When R and/or $R_1$ is H in the formula I compounds tautomers occur and are included. An illustrative example of such a tautomer is

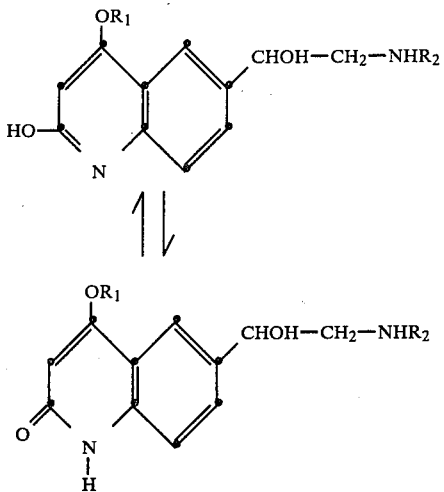

The compounds of formula I have one chiral center at the 1-position in the aminoethanol substituent and can have a second chiral center when the $R_3$ and $R_4$ substituents in the $R_2$ group are different. The chiral centers confer optical activity on the formula I compounds.

All the optical isomer forms, that is mixtures of enantiomers or diastereomers, e.g. racemates as well as individual enantiomers or diasteriomers of formula I are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

A compound of Formula I is useful for treating glaucoma since it decreases intraocular pressure when topically administered to the eye. The ability to lower intraocular pressure is determined using an in-vivo protocol in a rabbit model.

Said compound is preferably administered in the form of an opthalmic pharmaceutical composition adapted for topical administration to the eye such as a solution, an ointment or as a solid insert. Formulations of the compound may contain from 0.01 to 5% and especially 0.5 to 2% of medicament. Higher dosages as, for example, about 10% or lower dosages can be employed provided the dose is effective in lowering intraocular pressure. As a unit dosage form, between 0.001 to 5.0 mg., preferably 0.005 to 2.0 mg., and especially 0.005 to 1.0 mg. of the compound is generally applied to the human eye.

The pharmaceutical composition which contains the compound may be conveniently admixed with a non-toxic pharmaceutically organic carrier, or with a non-toxic pharmaceutical inorganic carrier. Typical of pharmaceutically acceptable carriers are, for example, water, mixtures of water and water-miscible solvents such as lower alkanols or aralkanols; vegetable oils; polyalkylene glycols; petroleum based jelly; ethyl cellulose; ethyl oleate; carboxymethylcellulose; polyvinylpyrrolidone; isopropyl myristate, and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000 bacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetate, glyconate buffers, and other conventional ingredients such as sorbitan monolaurate, triethanolamine, oleate, polyoxyethylene sorbitan monopoalmitylate, dioctyl sodium sulfosuccinate, monothioglycerol, thiosorbitol, ethylenediamine tetracetic acid, and the like. Additionally, suitable opthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates and as polyacrylic acid salts; natural products such as gelatin, alginates, pectins, tragacanth, karaya, chondrus, agar, acacid; the starch derivatives such as starch acetate, hydroxyethyl starch ethers, hydroxypropyl starch, as well as other synthetic derivatives such as poly vinyl alcohol, polyvinyl pyrrolidone, polyvinyl methyl ether, polyethylene oxide, neutralized carbopol and xanthan gum, and mixtures of said polymer.

Preferably the solid insert is prepared from cellulose derivatives such as methylcellulose, hydroxyethyl cellulose, hydroxypropyl cellulose or hydroxypropylmethyl cellulose or from other synthetic materials such as polyvinyl alcohol, polyvinyl pyrrolidone, polyethylene oxide or polyvinyl methylether. Hydroxypropyl cellulose, one of the preferred polymers for the preparation of the insert is available in several polymeric forms, all of which are suitable in the preparation of these inserts. Thus, the product sold by Hercules, Inc. of Wilmington, Delaware under the name KLUCEL such as KLUCEL HF, HWF, MF, GF, JF, LF and EF which are intended for food or pharmaceutical use are particularly useful. The moleculare weight of these polymers useful for the purposes described herein may be at least 30,000 to about 1,000,000 or more. Similarly, an ethylene oxide polymer having a molecular weight of up to 5,000,000 or greater, and preferably 100,000 to 5,000,000 can be employed. Further, for example, PO-LYOX a polymer supplied by Union Carbide Co. may be used having a molecular weight of about 50,000 to 5,000,000 or more and preferably 3,000,000 to 4,000,000. Other specific polymers which are useful are polyvinyl pyrrolidine having a molecular weight of from about 10,000 to about 1,000,000 or more, preferably up to about 350,000 and especially about 20,000 to 60,000; polyvinyl alcohol having a molecular weight of from about 30,000 to 1,000,000 or more particularly about 400,000 and especially from about 100,000 to about 200,000; hydroxypropylmethyl cellulose having a molecular weight of from about 10,000 to 1,000,000 or more, particularly up to about 200,000 and especially about 80,000 to about 125,000; methyl cellulose having a molecular weight of from about 10,000 to about 1,000,000 or more, preferably up to about 200,000 and especially about 50 to 100,000; and CARBOPOL (carboxyvinyl polymer) of B. F. Goodrich and Co. designated as grades 934, 940 and 941. It is clear that for the purpose of this invention the type and molecular weight of the polymer is not critical. Any water soluble polymers can be used having an average molecular weight which will afford dissolution of the polymer and accordingly the medicament in any desired length of time. The inerts, therefore, can be prepared to allow for retention and accordingly effectiveness in the eye for any desired period. The insert can be in the form of a square, rectangle, oval, circle, doughnut, semi-circle, ¼ moon shape, and the like. Preferably the insert is in the form of a rod, doughnut, oval or ¼ moon. The insert can be readily prepared, for example, by dissolving the medicament and the polymer in a suitable solvent and the solution evaporated to afford a thin film of the polymer which can then be subdivided to prepare inserts of appropriate size. Alternatively the insert can be prepared by warming the polymer and the medicament and the resulting mixture molded to form a thin film. Preferably, the inserts are prepared by molding or extrusion procedures well known in the art. The molded or extruded product can then be subdivided to afford inserts of suitable size for administration in the eye.

The insert can be of any suitable size to readily fit into the eye. For example, castings or compression molded films having a thickness of about 0.25 mm. to 15.0 mm. can be subdivided to obtain suitable inserts. Rectangular segments of the cast or compressed film having a thickness between about 0.5 to 1.5 mm can be cut to afford shapes such as rectangular plates of 4×5–20 mm or ovals of comparable size. Similarly, extruded rods having a diameter between about 0.5 and 1.5 mm can be cut into suitable sections to provide the desired amount of polymer. For example, rods of 1.0 to 1.5 mm in diameter and about 20 mm long are found to be satisfactory. The inserts may also be directly formed by injection molding. It is preferred that the ophthalmic inserts containing the medicament of the present invention be formed so that they are smooth and do not have any sharp edges or corners which could cause damange to the eye. Since the term smooth and sharp edges or corners are subjective terms, in this application these terms are used to indicate that excessive irritation of the eye will not result from the use of the insert.

The ocular medicinal inserts can also contain plasticizers, buffering agents and preservatives. Plasticizers suitable for this purpose must, of course, also be completely soluble in the lacrimal fluids of the eye. Examples of suitable plasticizers that might be mentioned are water, polyethylene glycol, propylene glycol, glycerine, trimethylol propane, di and tripropylene glycol, hydroxypropyl sucrose and the like. Typically, such plasticizers can be present in the ophthalmic insert in an amount ranging from up to 1 about 30% by weight. A particularly preferred plasticizer is water which is present in amounts of at least about 5% up to about 40%. In actual practice, a water content of from about 10% to about 20% is preferred since it may be easily accomplished and adds the desired softness and pliability to the insert.

When plasticizing the solid medicinal product with water, the product is contacted with air having a relative humidity of at least 40% until said product picks up at least about 5% water and becomes softer and more pliable. In a preferred embodiment, the relative humidity of the air is from about 60% to about 99% and the contacting is continued until the water is present in the product in amounts of from about 10% to about 20%.

Suitable water soluble preservatives which may be employed in the insert are sodium bisulfate, sodium thiosulfate, ascorbate, benzalkonium chloride, chlorobutanol, thimerosal, phenylmercuric acetate, phenylmercuric borate, parabens, benzyl alcohol and phenylethanol. These agents may be present in amounts of from 0.001 to 5% by weight of solid insert, and preferably 0.1 to 2%.

Suitable water soluble buffering agents are alkali, alkali earth carbonates, phosphates, bicarbonates, citrates, borates and the like, such as sodium phosphate, citrate, borate, acetate, bicarbonate and carbonate. These agents may be present in amounts sufficient to obtain a pH of the system of between 5.5 to 8.0 and especially 7–8; usually up to about 2% by weight of polymer. The insert may contain from about 1 mg. to 100 mg. of water soluble polymer, more particularly from 5 to 50 mg. and especially from 5 to 20 mg. The medicament is present from about 0.1 to about 25% by weight of insert.

The ability of the Formula I compound to lower intraocular pressure is determined in rabbits with experimental glaucoma induced by intraocular injection of α-chymotrypsin. Compounds of Formula I are effective in lowering intraocular pressure after topical application. Pressure is reduced in the normal and the glaucomatous eye.

The compounds (Formula I) of the present invention have β-adrenergic blocking activity. This β-adrenergic blocking activity is determined by measureing the ability of representative compounds to block the β-adrenergic stimulant effect of isoproterenol in a test animal.

The compounds of the present invention also have α-adrenergic blocking activity. This α-adrenergic blocking activity is determined, (a) in vitro by measureing the ability of a representative Formula I compound to displace radio labeled α-adrenergic antagonist from a tissue substrate or (b) in vivo, by measuring the ability of representative Formula I compound pyridines to block the α-adrenergic stimulant effect of phenylephrine in anesthetized normotensive animals.

The present compounds exhibit antihypertensive activity of immediate onset. This rapid onset antihypertensive activity is determined by administering a representative compound of the present invention to spontaneously hypertensive (SH) rats and measuring the effect on blood pressure.

The α- and β-adrenergic blocking activity of the present compounds indicates that the compounds may be useful in humans for treating cardiovascular conditions susceptible to β-blockage therapy (e.g., angina pectoris, arrhythmia) while minimizing bronchoconstriction via α-adrenergic blockage. This α/β-blockage effect can be useful in treating hypertension caused by pheochromocytoma.

For use as α/β-adrenergic blocking agents, and/or antihypertensive agents the compounds of the present invention can be administered orally, by inhalation, by suppository or parenterally, i.e., intravenously, intraperitoneally, etc. and in any suitable dosage form. The compounds may be offered in a form (1) for oral administration, e.g., as tablets in combination with other compounding ingredients (diluents or carriers) customarily used such as talc, vegetable oils, polyols, benzyl alcohols, starches, gelatin and the like—or dissolved, dispersed or emulsified in a suitable liquid carrier—or in capsules or encapsulated in a suitable encapsulating material, or (2) for parenteral administration, dissolved, dispersed, or emulsified in a suitable liquid carrier or diluent or (3) as an aerosol or (4) as a suppository. The ratio of active ingredient (present compound) to compounding ingredients will vary as the dosage form required. Conventional procedures are used to prepare the pharmaceutical formulations. The effective daily dosage level for the present compounds for applications other than treatment of the eye may be varied from about 10 mg to about 3000 mg. Daily doses ranging from about 100 to about 2500 mg are preferred, with about 200 to about 1000 mg being a more preferred range. Oral administration is preferred. Either single or multiple daily doses may be administered depending on unit dosage.

Compounds of formula I also have bronchodilator activity. This is determined by measuring the effectiveness of the compound to antagonize the contractile slow reacting substance of anaphylaxis (SRS-A). The compounds are thus useful to treat conditions in mammals especially human beings which benefit from bronchodilator, the compound is administered orally or parenterally in conventional dosage form such as tablet, capsule, solution, dispersion, emulsion or an aerosol using an appropriate delivery device and formulation. The oral route is preferred.

Sufficient formula I compound is administered to produce the desired level of bronchodilation. Daily dosages for oral or parenteral administration may range from about 1 mg to about 300 mg, and preferably from about 2 to about 150 mg. Spray or aerosol delivery will be in metered doses ranging from about 50 to about 1000 mcg, administered as needed.

Thus, other embodiments of the present invention are the pharmaceutical compositions containing a therapeutically effective amount of the Formula I compound and methods for treating various conditions.

Compounds of formula I may be prepared by any convenient process. Useful processes are illustrated by the following set of reaction equations:

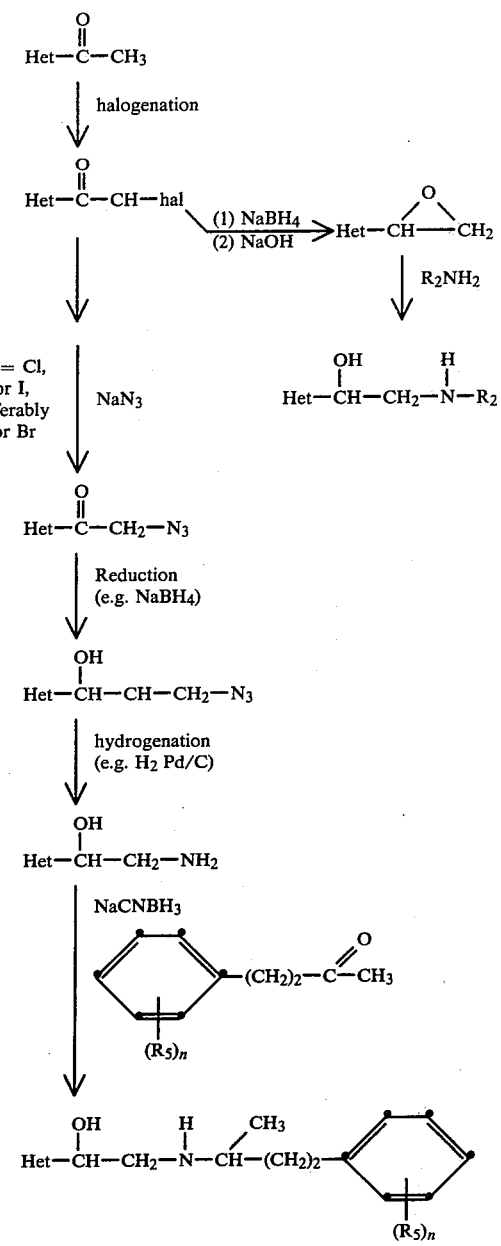

The following examples illustrate the preparation of compounds of formula I. Temperatures are in degrees Celsius.

EXAMPLE 1

6-[(2-Amino-1-hydroxy)ethyl]-2-ethoxy-4-methoxyquinoline maleate

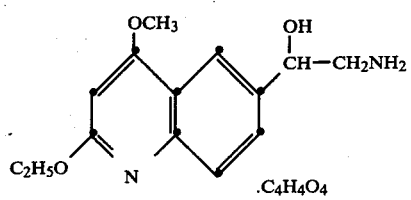

(a) 6-Acetyl-2-ethoxy-4-hydroxyquinoline A

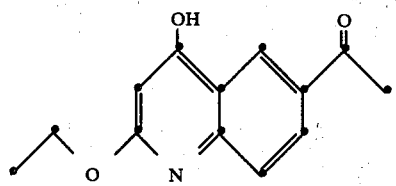

A mixture of 14.5 gm. (0.107 moles) of p-aminoacetophenone and 19.0 gm. (0.097 moles) of ethyl (1-ethoxyformimidoyl)acetate hydrochloride (Chem. Ber., 100, 1428 (1967)) in 500 ml. of dry $CH_2Cl_2$ was stirred at 22° C. for 18 hours. The reaction, containing a precipitate of $NH_4Cl$, was washed successively with ice cold aqueous solutions of 1 N HCl (2×100 ml), in $Na_2CO_3$ (2×100 ml) and saturated NaCl, and dried over $Na_2SO_4$. Filtration and evaporation yielded 20 gm. of crude ethyl [1-ethoxy(N-p-acetylphenyl)formimidoyl]acetate. This crude material was stirred and heated at 250° in 150 ml. of Dowtherm A for 30 minutes. Cooling dilution with 400 ml. of 1:1 ether-hexane and filtration of the precipitate yielded 12 gm. of the title compound. By base extraction of the filtrate and acidification, a further 2.5 gm. of product was obtained, mp. 210°–219° C. (65% yield).

Analytical sample (MeOH) m.p. 242°–243° C.

(b) 6-Acetyl-2-ethoxy-6-methoxyquinoline B

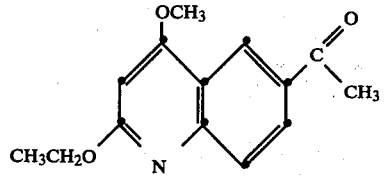

A mixture of 46.2 gm. (0.2 mole) of A, 42.6 gm. (0.3 moles) of methyl iodide and 54.8 gm. (0.4 moles) of $K_2CO_3$ in 800 ml. of acetone was heated to reflux for 4 hours. After evaporation of the solvent, the residue was taken up in 1600 ml. of methylene chloride and 800 ml. of water. After separation of layers, the organic phase was extracted with 2×400 ml. 1 N NaOH, 2×400 ml. $H_2O$ and dried over $MgSO_4$. After filtration and evaporation the residue was treated with 1000 ml. hot methanol, filtered hot, and the filtrate concentrated to 500 ml. Upon cooling and filtration there was obtained 30.2 gm. (62%) of B, m.p. 137°–140° C.

Analytical sample (MeOH), m.p., 138.5°–139.5° C.

(c) 6-Azidoacetyl-2-ethoxy-4-methoxyquinoline C

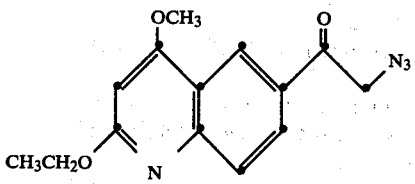

To a solution of 4.91 gm. (20 mmoles) of B in 270 ml. of acetic acid and 75 ml. of ether, cooled to 10° C., was added gaseous HBr in excess. A solution of 3.4 gm. (21 mmoles) of bromine in 75 ml. acetic acid was added over 75 min. The resulting mixture was stirred for 1 hour at 22° C., evaporated and the residue stirred with 150 ml. of 10% $NaHCO_3$. The aqueous suspension was extracted with 3×200 mls. of $CHCl_3$ and after drying and evaporation of the organic extracts there was obtained 6.57 gm. of crude 6-bromo-acetyl-2-ethoxy-4-methoxy quinoline. This material was dissolved in 150 ml. of dimethylformamide and to the solution was added a solution of 1.95 gm. (30 mmoles) of sodium azide in 35 ml. of $H_2O$. The solution temperature rose from 22° C. to 35° C. and after 105 minutes had fallen back to 25° C. The mixture was diluted with 1500 ml. of water and extracted with 3×300 ml. of $CHCl_3$. After washing the organic extracts with water (3×200 ml.), drying and evaporation, there was obtained 5.95 gm. of crude solid. This was dissolved in 75 ml. of ethyl acetate, 50 ml. of hexane was added, and after refrigeration and filtration, there was obtained 4.88 gm. (85%) of c, m.p. 129°–132° C.

Analytical sample (EtOAc-hexane), m.p. 133.5°–134° C.

(d) 6-[(2-Amino-1-hydroxy)ethyl]-2-ethoxy-4-methyloxyquinoline maleate D

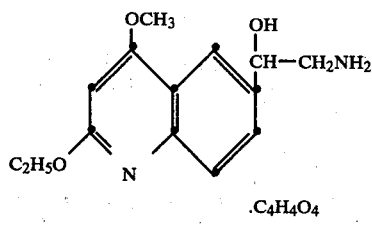

To a suspension of 14.3 gm. (50 mmoles) of C in 800 ml. of ethanol was added 33.8 gm. (150 mmoles) of $SnCl_2.2H_2O$ and 50 ml. of 12 N HCl. After warming at 50° for 2 hours, the reaction mixture was refrigerated, and filtration of the mixture gave 29.5 gm. of a crystalline salt. This salt was dissolved in 600 ml. of water and 15 ml. of 12 N HCl, and treated three times with an excess of $H_2S$ gas, filtering off the precipitated tin sulfides each time. Evaporation of the aqueous filtrate left 13.9 gm. of the hydrochloride salt of 6-aminoacetyl-2-ethoxy-4-methoxyquinoline.

The above salt was dissolved in a mixture of 50 ml. of water and 550 ml. of isopropanol, and to this solution 7.67 gm. (200 mmoles) of sodium borohydride was added over 30 minutes with stirring. After 3 hours stirring at 23° C., the solution was adjusted to pH 3 by addition of 12 N HCl and evaporated to dryness. The residue was taken up in 150 ml. of water and made basic (pH 10) by addition of 10% NaOH. Extraction with 4×150 ml. of ethyl acetate, drying of the organic extracts, and evaporation gave 9.6 gm. (72%) of D as the free base which was recrystallized from 50 ml. of $CH_2Cl_2$-hexane to give 9.2 gm. (70% overall), m.p. 114°–115° C.

The maleate salt was prepared in ethyl acetate from 1049 mg. (4 mmoles) of the free base and after recrystallization from EtOAc-MeOH, there was obtained 1.33 gm. (88%) of D, m.p. 162°–163° C. (dec.).

EXAMPLE 2

6-[(2-amino-1-hydroxy)ethyl]-2,4-dihydroxyquinoline hydrochloride E

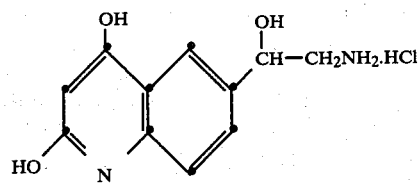

A solution of the free base of D, Example I (2.62 gm., 10 mmoles) in 100 ml. of 6 N HCl was heated to reflux for 26 hours, evaporated to dryness and 2×25 ml. of water evaporated from the residue to remove the bulk of the HCl. to leave a light yellow solid. This solid was taken up in 100 ml. of ethanol, filtered to remove insolubles and concentrated to about 10 ml. cooling deposited 1.87 gm. of yellow solid. This was again dissolved in 200 ml. of ethanol and treated twice with 1 gm. of charcoal. Concentration to 15 ml. and dilution with 50 ml. of ethyl acetate precipitated 1.69 gm. (66%) of the E compound as a cream solid, m.p. 360° C. (dec.).

EXAMPLE 3

6-[2-(1-methyl-3-phenylpropylamino)-1-hydroxyethyl]-2-ethoxy-4-methoxyquinoline maleate F

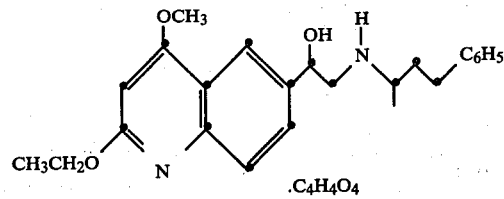

A solution of the free base amine from Example 1, step D (5.51 gm., 21 mmoles), benzylacetone (3.42 gm. 23 mmoles) and NaCNBH$_3$ (1.45 gm., 23 mmoles) in 105 ml. of methanol was stirred over 10.5 gm. of 4 A molecular sieves at 22° C. for 72 hours. To the solution was added 12 N HCl until it was strongly acidic, and after filtration from the molecular sieves, it was evaporated to dryness. The residue was dissolved in 200 ml. of water, the solution extracted with 3×55 ml. of ether and the aqueous phase made basic with 15% Na$_2$CO$_3$. The aqueous was then extracted with 3×70 ml. of ethyl acetate and the organic extracts washed with water dried and evaporated and the resulting gummy residue (8.8 gm.) chromatographed over 415 gm. of silica using 12:1 chloroform-methanol as eluant. There was obtained 7.9 gm. of an amber gum, which was crystallized from ether-hexane to give 7.4 gm. (89%) of the free base of the F compound, m.p. 90°–98° C.

The maleate salt was prepared in ethylacetate from 1.18 gm. (3 mmoles) of the free base and 348 mg. (3 mmoles) of maleic acid. After two crystallizations from ethyl acetate-ether there was obtained 1.12 gm. (78%; overall yield 69%) of the title compound, m.p. 122°–126° C.

EXAMPLE 4

6-[2-(1-methyl-3-phenylpropylamino)-1-hydroxyethyl]-2,4-dihydroxyquinoline hydrochloride G

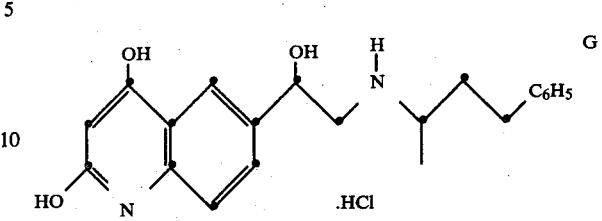

A solution of 2.82 gm. (7.2 mmoles) of the free base from Example III in 150 ml. of 8 N HCl was heated at 105° C. under an argon atmosphere for 24 hours, cooled, filtered from a small amount of insoluble material, and evaporated to dryness to leave 2.85 gm. of a foamy yellow solid. Treatment with charcoal (3×1 gm.) in 100 ml. of methanol, evaporation of the methanol, and slurrying the residue with ethyl acetate (3×100 ml.), left 1.58 gm. of the G compound as a light yellow solid, m.p. 360° C.

Claims to the invention follow.

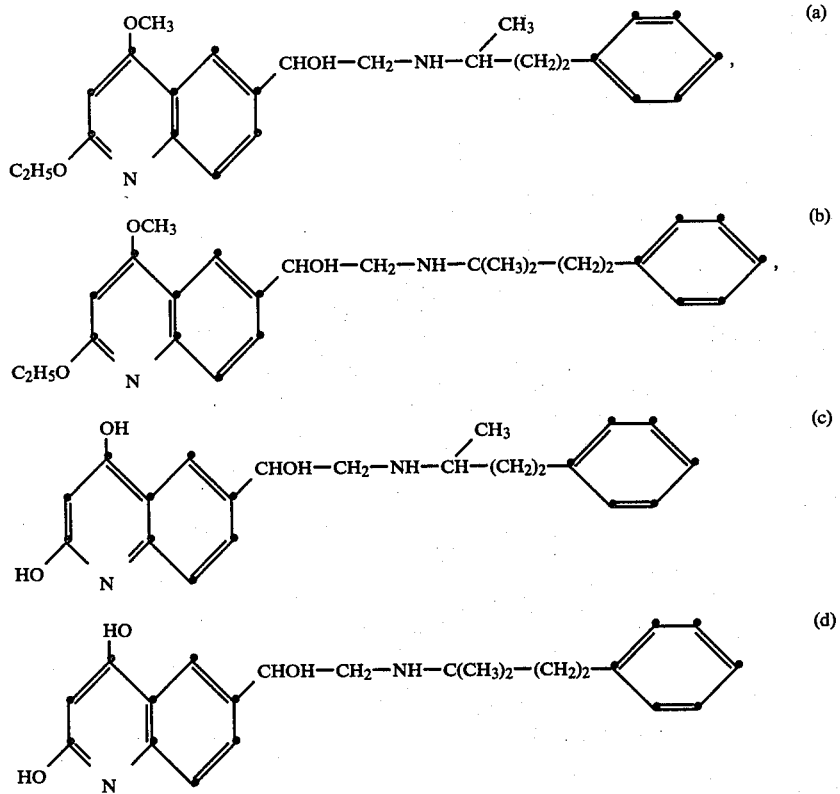

What is claimed is:

1. Compounds of the formula:

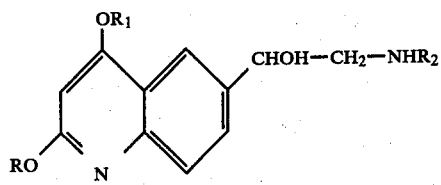

tautomers, pharmaceutically acceptable salts and individual isomers thereof wherein R and R$_1$ are independently selected from H and C$_1$–C$_3$ alkyl and R$_2$ is

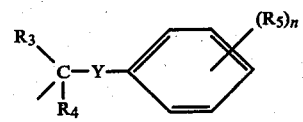

wherein

R$_3$ and R$_4$ are independently selected from H and C$_1$–C$_3$ alkyl,

R$_5$ is H, OH, O—CH$_{1-3}$ alkyl, halogen or C$_{1-3}$ alkyl

Y is CH$_2$, (CH$_2$)$_2$, (CH$_2$)$_3$, (CH$_2$)$_4$ or —CH$_2$O— and n is 1 or 2.

2. The compounds of claim 1 wherein Y is CH$_2$ or (CH$_2$)$_2$.

3. The compounds of claim 1 wherein Y is (CH$_2$)$_2$.

4. The compounds of claim 3 wherein R$_3$ and R$_4$ are H or CH$_3$.

5. The compounds of claim 4 wherein R$_3$ is H.

6. The compounds of claim 4 wherein R$_3$ and R$_4$ are each CH$_3$.

7. The compounds of claim 4 wherein R$_5$ is H or OCH$_3$.

8. The compounds of claim 7 wherein R$_2$ is

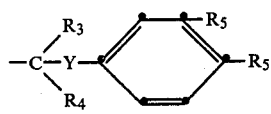

9. Compounds of claim 8 wherein $R_5$ is $OCH_3$.

10. Compound of claim 1 having the formula

11. Compounds of claim 10 formula (a) or (c).

12. A pharmaceutical composition for (1) treating hypertension (2) reducing intraocular pressure or (3) effecting bronchodilation containing an effective amount of a compound of claim 1.

13. A method of (1) treating hypertension (2) reducing intraocular pressure or (3) effecting bronchodilation by administering an effective amount of claim 1 compound in suitable dosage form.

* * * * *